(12) United States Patent
Bansal et al.

(10) Patent No.: US 6,439,456 B1
(45) Date of Patent: *Aug. 27, 2002

(54) METHOD FOR TRANSFERRING MONEY

(76) Inventors: Pradeep K. Bansal, 44 Edwina Ct., Dayton, NJ (US) 08810; Lee Begeja, 12 Dunbridge La., Gillette, NJ (US) 07933; Jeffrey Joseph Farah, 17 Princess Dr., North Brunswick, NJ (US) 08902; Rajesh Kapadia, 79 Bradford La., Plainsboro, NJ (US) 08536; John Gerow Ramage, 200 Wychwood Rd, Westfield, NJ (US) 07090; Benjamin J. Stern, 45 Dorothy Dr., Morristown Township, NJ (US) 07960

(*) Notice: Subject to any disclaimer, the term of this patent is extended or adjusted under 35 U.S.C. 154(b) by 0 days.

This patent is subject to a terminal disclaimer.

(21) Appl. No.: 09/814,859

(22) Filed: Mar. 23, 2001

Related U.S. Application Data

(63) Continuation of application No. 09/219,373, filed on Dec. 23, 1998, now Pat. No. 6,206,283.

(51) Int. Cl.⁷ .............................................. G06F 17/60
(52) U.S. Cl. ........................ 235/379; 235/380; 455/558; 705/42; 705/44
(58) Field of Search .................................. 235/379, 380, 235/382; 455/558, 407, 575; 705/35, 41, 42, 43, 44

(56) References Cited

U.S. PATENT DOCUMENTS

| | | | | |
|---|---|---|---|---|
| 5,559,887 A | | 9/1996 | Davis et al. .................... 380/24 |
| 5,590,038 A | * | 12/1996 | Pitroda ......................... 235/380 |
| 5,650,604 A | * | 7/1997 | Marcous et al. ............. 235/379 |
| 5,691,525 A | * | 11/1997 | Aoki et al. ................... 235/379 |
| 5,748,737 A | | 5/1998 | Daggarr ......................... 380/24 |
| 5,778,067 A | * | 7/1998 | Jones et al. .................. 235/379 |
| 5,886,333 A | * | 3/1999 | Miyake ......................... 235/380 |
| 5,915,226 A | | 6/1999 | Martineau .................... 455/558 |
| 6,058,382 A | * | 5/2000 | Kasai et al. ................... 705/41 |
| 6,206,283 B1 | * | 3/2001 | Bansal et al. ................ 235/379 |

* cited by examiner

*Primary Examiner*—Karl D. Frech
*Assistant Examiner*—Daniel St. Cyr

(57) ABSTRACT

A method for transferring money is described. This method can include providing a cash card having stored thereon an amount of money; making a telephone call to a predetermined telephone number using the cash card as a payment device for the telephone call; dialing a predetermined suffix to the predetermined telephone number followed by a desired dollar amount; debiting the cash card by the desired dollar amount; and, crediting an account associated with the predetermined telephone number by the desired dollar amount.

11 Claims, 1 Drawing Sheet

10

METHOD FOR TRANSFERRING MONEY

This application is a Continuation of application Ser. No. 09/219,373, filed Dec. 23, 1998, now U.S. Pat. No. 6,206,283 B1, which is incorporated herein, in its entirety, by reference.

BACKGROUND OF THE INVENTION

The present invention relates generally to methods and apparatuses for transmitting money electronically, and more particularly to a method and apparatus for transmitting money electronically via a third party.

Many electronic cash payment cards and methods have been proposed to transfer value from an individual to a merchant and/or from an individual to another individual. Each of these systems requires a complex series of transactions and verifications to ensure that the overall transaction occurs securely—so much so, that many individuals refuse to employ them. This is often cited as a reason that electronic commerce has not yet reached the levels many expected.

One technique for transferring money electronically is for both sides of the transaction to transfer the money to an intermediary, often termed a trusted entity. Usually, this involves a series of pre-transaction arrangements that must be performed to establish the relationship with the intermediary. Once a party has established a relationship with the intermediary then the party can transmit money electronically between any other party that has similarly established a relationship with the intermediary by using the procedures established by the intermediary. Often, however, establishing these relationships is time consuming and requires the submission of more documentation than many individuals prefer. Furthermore, this requires both parties to use the same intermediary.

The present invention is therefore directed to the problem of developing a method and apparatus for transmitting money electronically that achieves a user's desired level of security, yet enables non-sophisticated users to employ it without requiring the submission of substantial documentation by either party to the transaction.

SUMMARY OF THE INVENTION

The present invention solves this problem by providing a method for transferring money electronically that includes the steps of providing a telephone card having stored thereon an amount of money, making a telephone call to a predetermined telephone number using the telephone card as a payment device for the telephone call, dialing a predetermined suffix to the predetermined telephone number followed by a desired dollar amount, debiting the telephone card by the desired dollar amount and crediting an account associated with the telephone number by the desired dollar amount.

According to one exemplary embodiment of the method of the present invention the telephone card can be used to activate the telephone.

According to another exemplary embodiment of the method of the present invention, the telephone includes a wireless or wireline telephone.

According to yet another exemplary embodiment of the method of the present invention the telephone card comprises a MONDEX style card combined with an individual telephone card.

According to yet another exemplary embodiment of the method of the present invention the predetermined suffix includes DTMF keys 2274, (or 4358) and the desired dollar amount is enclosed in delimiters, such as either the asterisk symbol "*" or the number symbol "#."

According to yet another exemplary embodiment of the method of the present invention the predetermined suffix includes DTMF tones resulting from pressing keys on the telephone keypad representing an alpha sequence "CASH" or the equivalent in another language.

Another aspect of the present invention includes a method for transferring money electronically that includes the steps of making a telephone call to a predetermined telephone number using a credit card associated with a user's account as a payment device for the telephone call, entering a predetermined suffix after the predetermined telephone number followed by a desired dollar amount, and debiting the user's account by the desired dollar amount, and/or crediting an account associated with the telephone number by the desired dollar amount.

Another aspect of the present invention includes a method for transferring money electronically that includes the steps of making a telephone call to a predetermined telephone number using an electronic cash card as a payment device for the telephone call, which electronic cash card has stored thereon a certain amount of money, entering a predetermined suffix after the predetermined telephone number followed by a desired dollar amount, and deducting the desired dollar amount from the electronic cash card, and/or placing a credit in the desired dollar amount on an account associated with the telephone number.

Another aspect of the present invention includes a method for transferring money electronically that includes the steps of inserting a first electronic cash card into a first telephone, wherein the first electronic cash card has stored thereon a certain amount of money, inserting a second electronic cash card into a second telephone, making a telephone call to the second telephone using the electronic cash card as a payment device for the telephone call, dialing a predetermined suffix to a telephone number of the second telephone followed by a desired dollar amount, and transferring the desired dollar amount from the first electronic cash card to the second electronic cash card.

According to an exemplary embodiment of the present invention, the method includes the step of linking an identity of a caller to a cash account, and placing a resulting transaction on a statement to the cash account.

According to yet another exemplary embodiment of the present invention, the method includes the step of linking an identity of a caller to a user's account, and placing a resulting transaction on the user's telephone bill.

According to an exemplary embodiment of the present invention, the method includes the step of speaking the amount into an automated speech recognition system coupled to a database linking the identity of the caller to a cash account.

Another aspect of the present invention is apparatus for transferring money electronically between two parties that includes a first user card storing an amount of money and a second user card including a rewritable media. A first telephone has a card reader reading the amount of money on the user card upon insertion of the user card into the card reader. In this apparatus, a first user enters a predetermined sequence of dial tones to indicate a cash transaction is to take place followed by a particular sequence of dial tones indicating a particular amount of money to transfer. The apparatus also includes a second telephone including a second card reader writing the particular amount of money to the second user card upon insertion of the second user card into the second card reader and upon receiving the predetermined sequence of dial tones and the particular sequence of dial tones.

According to an exemplary embodiment of the present invention, the apparatus includes a communications network being coupled to the telephone and transferring the predetermined and particular sequences of dial tones pressed by a first user operating the first telephone to the second telephone thus controlling the second telephone and the second card reader.

According to another exemplary embodiment of the present invention, the first telephone is a wireless telephone.

According to an exemplary embodiment of the present invention, the first user card comprises a MONDEX style card combined with an individual telephone card.

According to an exemplary embodiment of the present invention, the apparatus includes an automated speech recognition system recognizing a voice of the first user and authorizing the transaction.

According to an exemplary embodiment of the present invention, the apparatus includes a billing system being coupled to the communications network and billing an account of the first user and crediting an account of the second user.

DETAILED DESCRIPTION

Figure 1:
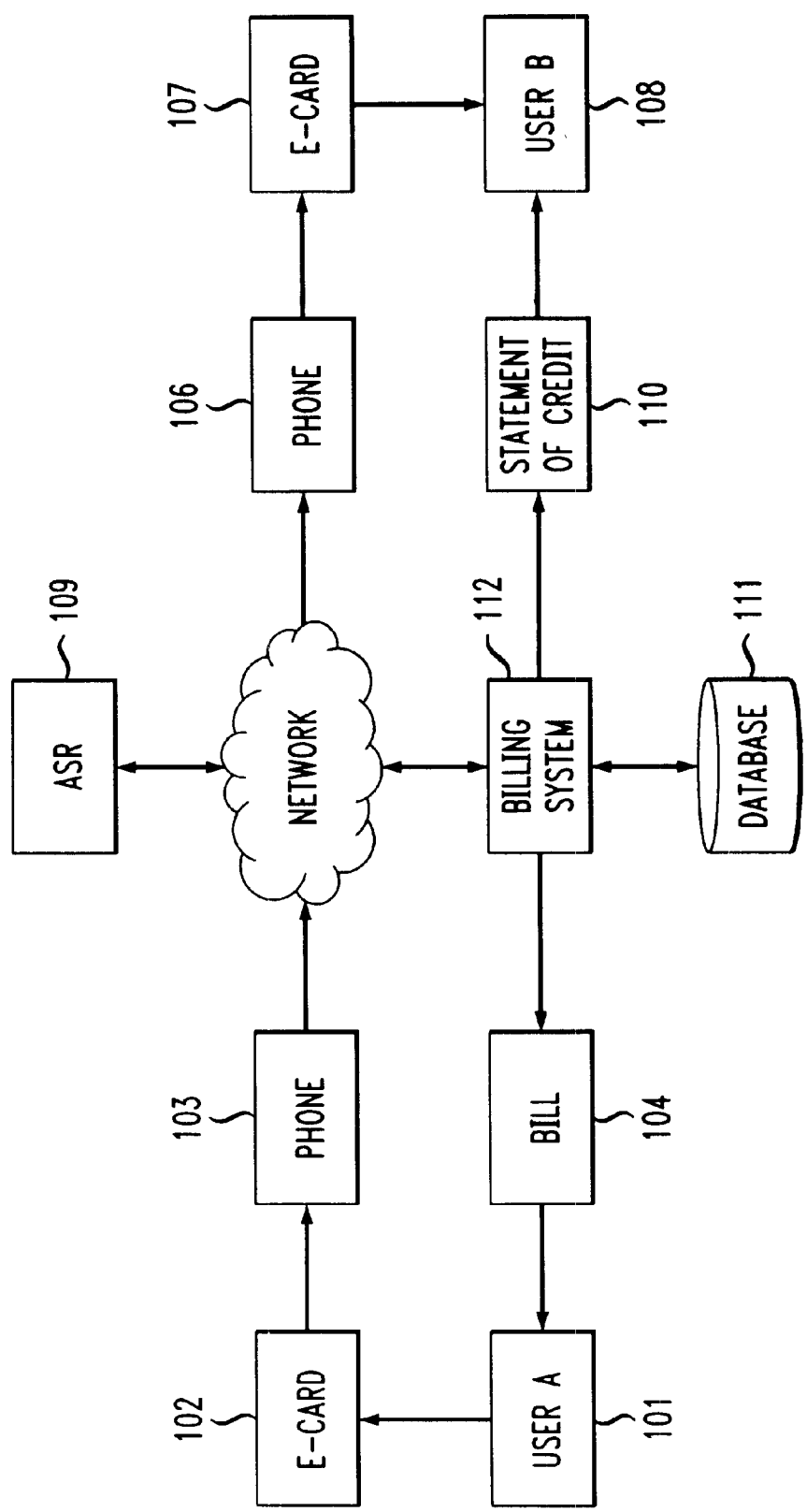
FIG. 1 depicts an exemplary embodiment of a system according to the present invention.

The present invention provides a simple and secure way, for an individual 101 to transfer money from a cash card 102 (or the account that the cash card is tied to) by making a telephone call, e.g., a wireless telephone call, via telephone 103 over a network 105 (which, e.g., could be a wireless network) to another individual or entity 108 connected to the network 105 via a telephone 106 and cash card 107. The present invention operates with either a wireless or wireline telephone. The information could be transferred from the user's wireless telephone using touch tones, for example, or any other wireless protocol, such as a protocol being used to communicate with the Mobile Switching Center (MSC). One such example used in Personal Communication Services (PCS) is IS-41 Management Application Protocol (MAP).

One exemplary embodiment of the present invention combines a MONDEX style card with the individual phone cards that are currently in use in Europe with GSM phones. This electronic cash ("ecash") ecash/phone card 102 is inserted into the phone 103 to activate the phone 103 for billing use and serves as the basis for a cash transaction. The electronic cash card, another example of which can be a smart card, includes a magnetic strip (or some other alterable media), which is readable by a magnetic strip reader, for example. Alternatively, the electronic cash card can have a memory chip on it, which enables reading and writing to the memory chip.

One exemplary embodiment of the method of the present invention works as follows. Assume that person A 101 makes a telephone call to person B 108 and dials a suffix to the number to indicate the transaction and the amount. In this case, one could transfer money to another card 107 or account holder from one's card 102 by dialing their number followed by #CASH#200# to transfer 200 dollars to the other account, for example. Alternatively, the user could enter the word for "cash" in another language (e.g., the language of the country in which the Mobile Switching Center is located that processes the call), such as "GELT" or "4358." The card 107 is then capable of being used as a cash card to make purchases or as a phone card to make calls. A database 111 links the identity of the caller to the cash account and the transaction appears as part of a bank statement 110 or as part of a wireless phone bill 104 from a billing system 112 of the network 105.

As an example, one way to ensure the security of the above money transaction is to use the existing digital protocols that are currently used ensure the security of the billing records to authenticate the money transaction itself. In other words, the present invention takes advantage of the fact the digital protocols are in use to protect the transfer of information between a wireless telephone and the Mobile Switching Center. Some of these protocols perform encryption of the billing codes and dialed numbers, which ensure the security of the wireless telephone.

Alternatively, a user could use his wireless phone to dial an account number and transfer money by entering the amount via DTMF or by speaking the amount to an automated speech recognition (ASR) application 109 connected to the database 111.

As another alternative, a user 101 could also use the phone 103 to make purchases via the card 102 by just dialing a number and having an anonymous purchase made of the item. Since the user 101 would be identified by the wireless network 105, the user 101 would not have to enter any additional information about identification or credit card. The number that the user dialed (phone 106) could then debit the user's card 102 directly (or simply bill the user via the telephone bill) and the item could be delivered without any need for the user to enter more information.

One exemplary embodiment of the present invention uses a button on the telephone itself, such as a button having a dollar symbol ($) on it, that when pressed transfers codes to the Mobile Switching Center to indicate that the telephone call is a money transfer. Then, by pressing the $ button, followed by a numerical sequence, a user could easily perform a secure electronic money transfer.

It should be noted that the present invention also enables two parties to a cash transaction to remain anonymous. The only fact that is known is that a transaction has occurred. Given specific types of transactions, e.g., cash transfers, the anonymity of the transferor and the recipient of the cash will be maintained. Billing statements will simply indicate that a call has taken place between two parties in which a transaction has also occurred. In this case, the specific type will not be identified. Thus, it is possible using the present invention to maintain the anonymity of the parties to the transaction, as in a cash transfer.

The present invention also provides a simple, straightforward way to enable currency translation as part of the cash transfer. The barriers to transactions involving different currencies are formidable, involving considerable time, expense and the likelihood of error on the part of the intermediaries. The present invention serves as a substitute for the currency translation services now provided to a single individual by a bank, for example. Here, the present invention would mostly serve as a convenience, since the individual would not go physically to a bank that provides this specialty service, and would not need to carry potentially significant sums of money in the foreign currency on his/her person after the transaction.

Further, the present invention could transfer cash involving a currency translation between two parties, quite possibly in different countries, without substantial bureaucracy normally involved, without the burdensome fees, and without multiple intermediaries that currently engender errors and failures in the process. The process would enable transactions of relatively small size that are currently not cost-effective, and would enable person-to-person transactions that are not currently feasible. One example of this process is as follows. The user dials an international number, and performs the above described cash transaction. By assuming the currency desired for each party is the currency of the place where the transferor and recipient are located, the system converts the currency from one type to another as part of the process of debiting the transfetror's account and crediting the recipient's account. For example, a user in the United States who dials a telephone number in France, and enters the cash transaction described above, would have his account debited in U.S. dollars by the amount keyed into the telephone, while the recipient in France would have his account credited by an amount equal in French francs to the amount in dollars keyed in by the transferor. In this case, the country codes can be used to indicate the currency into which the cash is to be converted, assuming that the amount being entered is represented in the currency of the country in which the call is being made.

To accomplish this, the present invention employs a database at the billing center that maintains a current exchange rate for all tradeable currencies. When the cash transfer occurs, the database is searched for the appropriate exchange rate, which is used to convert from one currency to the next. The conversion is relatively straightforward, and simply results in the system debiting one account by the desired amount in one currency and crediting another account by an amount in a different currency, which is equivalent at the time the transaction occurs to the desired amount in the first currency. For example, using the U.S./French example again, if a user in the United States wants to transfer U.S. $200 to an individual in France, the user dials the telephone number of the individual and keys in the transfer as #CASH#200#. The system recognizes this as a cash transfer from U.S. currency to French currency (based on the dialed country code). The system then converts the U.S. $200 to the appropriate amount in Francs. Then, the system debits the account of the U.S. user by U.S. $200 and credits the account of the individual in France by the appropriate amount in Francs.

Alternatively, the user could after making the telephone call, enter indicate that a transfer from one currency to another is desired by entering a predetermined sequence of keys, such as #CASH#200#CONV#US#FR#, in which US=country code for United States, and FR=country code for France. Alternatively, the system could recognize these codes (i.e., US, FR) and identify them as the appropriate country. This command would first indicate that a cash transfer was to occur, which also involved a currency conversion from the first listed currency to the second listed currency.

The foregoing description shows only the preferred embodiments of the present invention. Various modifications are apparent to those skilled in the art without departing from the scope and spirit of the present invention. Therefore, the embodiments shown should be considered to be illustrative, not in any manner restrictive.

What is claimed is:

1. A method for transferring money electronically using a cash card having an amount of money associated with the card, the method comprising:

receiving notification of a telephone call made to a predetermined telephone number;

receiving signals corresponding to a dialed predetermined suffix to the predetermined telephone number;

receiving a desired dollar amount;

debiting the cash card by the desired dollar amount; and crediting an account associated with the predetermined telephone number by the desired dollar amount.

2. The method according to claim 1, further comprising:

activating a telephone in response to an indication that the cash card was inserted into the telephone.

3. The method according to claim 1, wherein the predetermined suffix includes Dual Tone Multi-Frequency signals corresponding to keys 2274, and the desired dollar amount is enclosed in delimiters.

4. The method according to claim 1, wherein the predetermined suffix includes Dual Tone Multi-Frequency signals corresponding to keys 4358, and the desired dollar amount is enclosed in delimiters.

5. The method according to claim 1, wherein the predetermined suffix includes Dual Tone Multi-Frequency signals corresponding to keys on a telephone keypad representing an alpha sequence "CASH."

6. A method for transferring money electronically, comprising:

receiving notification of a telephone call to a predetermined telephone number, the payment device for the call being a credit card associated with a user's account;

receiving a predetermined suffix after the predetermined telephone number followed by a desired amount;

debiting the user's account by the desired amount; and, crediting an account associated with the predetermined telephone number by the desired dollar amount.

7. The method according to claim 1, further comprising:

interpreting a predetermined suffix received after the desired amount to indicate that the amount listed is to be converted from one currency to another, the suffix including an identification of a currency in which the desired amount is to be converted.

8. The method according to claim 1, further comprising:

detecting a dialed country code and using the dialed country code to determine a currency into which the desired amount is to be converted.

9. The method according to claim 6, further comprising:

determining a country in which the telephone call originates and denominating the desired amount in a currency of the country.

10. The method according to claim 6, further comprising:

converting the money to be transferred from a first currency to a second currency and debiting the user's account by the desired dollar amount in a first currency and crediting an account associated with the dialed telephone number by an amount in the second currency equivalent to the desired amount in the first currency.

11. A method for transferring money electronically, comprising:

receiving a telephone call made to a predetermined telephone number using an electronic cash card as a payment device for the telephone call, the electronic cash card having stored thereon an amount of money;

receiving a predetermined suffix entered after the predetermined telephone number followed by a desired dollar amount;

deducting the desired dollar amount from the electronic cash card; and, crediting an account associated with the predetermined telephone number by the desired dollar amount.

* * * * *